(12) United States Patent
Holzhacker

(10) Patent No.: US 9,220,431 B2
(45) Date of Patent: Dec. 29, 2015

(54) ELECTRODE SYSTEM FOR TRANSDERMAL CONDUCTION OF ELECTRICAL SIGNALS, AND A METHOD OF USE THEREOF

(75) Inventor: Albert Holzhacker, São Paulo (BR)

(73) Assignee: Timpel S.A., Sao Paulo (BR)

( * ) Notice: Subject to any disclaimer, the term of this patent is extended or adjusted under 35 U.S.C. 154(b) by 307 days.

(21) Appl. No.: 13/132,300

(22) PCT Filed: Dec. 18, 2009

(86) PCT No.: PCT/BR2009/000414
§ 371 (c)(1),
(2), (4) Date: Aug. 15, 2011

(87) PCT Pub. No.: WO2010/069023
PCT Pub. Date: Jun. 24, 2010

(65) Prior Publication Data
US 2011/0288393 A1 Nov. 24, 2011

(30) Foreign Application Priority Data
Dec. 19, 2008 (BR) ..................................... 8053650

(51) Int. Cl.
*A61B 5/04* (2006.01)
*A61B 5/0408* (2006.01)
(Continued)

(52) U.S. Cl.
CPC ......... *A61B 5/04087* (2013.01); *A61B 5/04085* (2013.01); *A61B 5/0536* (2013.01);
(Continued)

(58) Field of Classification Search
CPC ............... A61B 5/6832; A61B 5/6801; A61B 5/04087; A61B 5/6833; A61B 5/04085; A61B 5/0006; A61B 5/0205; A61L 24/0031; A61N 1/0456; A61N 1/0492; A61N 1/36021; A61N 1/048; A61N 1/0472; A61N 1/0452; A61N 1/0484; A61N 2/008; A61N 1/04; A61N 1/0488

USPC ................. 600/372, 382–384, 386, 391–393, 600/508–509; 607/115, 119, 142, 148–149, 607/152
See application file for complete search history.

(56) References Cited

U.S. PATENT DOCUMENTS 4,067,342 A    1/1978  Burton
4,595,013 A *  6/1986  Jones et al. ................... 600/383
(Continued)

FOREIGN PATENT DOCUMENTS

BR    PI0704408    12/2009
CN    1946826      4/2007
(Continued)

OTHER PUBLICATIONS

International Search Report for PCT Application No. PCT/BR2009/000414, mailed Jun. 30, 2010.
(Continued)

*Primary Examiner* — Joseph Stoklosa
*Assistant Examiner* — Brian M Antiskay
(74) *Attorney, Agent, or Firm* — TraskBritt, P.C.

(57) ABSTRACT

There is disclosed a system of electrodes used for transdermal conduction of electrical signals and a method of use thereof, the system comprising a plurality of electrode parts connected by means of electrical conductors to electric impedance tomography apparatuses, as well as other devices, the parts being secured to an outer side of a flexible and porous blade coated on both sides thereof by layers of electrically conductive and adhesive materials, such electrically conductive and adhesive materials being in mutual contact through the pores of the blade, the inner face of the latter being removably secured, by means of adhesion, to the patient. The invention comprises means for positioning the electrode parts, as well as means for external protection thereof and of their respective conductors.

27 Claims, 8 Drawing Sheets

(51) Int. Cl.
  *A61B 5/053* (2006.01)
  *A61B 5/00* (2006.01)
  *A61N 1/04* (2006.01)

(52) U.S. Cl.
  CPC ............ *A61B5/6831* (2013.01); *A61N 1/0452* (2013.01); *A61N 1/0456* (2013.01); *A61N 1/0476* (2013.01); *A61N 1/0492* (2013.01); *A61B 2562/125* (2013.01)

(56) References Cited

U.S. PATENT DOCUMENTS

| | | | |
|---|---|---|---|
| 4,727,880 A * | 3/1988 | Roberts | 600/391 |
| 4,827,939 A * | 5/1989 | Cartmell et al. | 600/392 |
| 5,450,845 A | 9/1995 | Axelgaard | |
| 5,785,040 A | 7/1998 | Axelgaard et al. | |
| 5,813,981 A | 9/1998 | Carim | |
| 5,947,897 A | 9/1999 | Otake | |
| 6,788,979 B1 | 9/2004 | Axelgaard et al. | |
| 7,742,829 B2 | 6/2010 | Rainey | |
| 7,868,072 B2 | 1/2011 | Sasahara | |
| 8,527,028 B2 * | 9/2013 | Kurzweil et al. | 600/388 |
| 2002/0156357 A1 * | 10/2002 | Axelgaard | 600/391 |
| 2008/0281180 A1 * | 11/2008 | Choe et al. | 600/391 |
| 2009/0084674 A1 * | 4/2009 | Holzhacker et al. | 204/286.1 |

FOREIGN PATENT DOCUMENTS

| | | |
|---|---|---|
| CN | 101180095 | 5/2008 |
| DE | 202004019971 U1 | 4/2005 |
| EP | 0855167 A1 | 7/1998 |
| WO | WO2007/070997 A1 | 6/2007 |

OTHER PUBLICATIONS

International Written Opinion for PCT Application No. PCT/BR2009/000414, mailed Jun. 30, 2010.
International Preliminary Report on Patentability for PCT Application No. PCT/BR2009/000414, mailed Jun. 21, 2011.
Search Report of the Chinese Application No. 200980151429.8, mailed Oct. 26, 2012.
Supplementary Search Report of the Chinese Application No. 200980151429.8, dated Mar. 6, 2014.

* cited by examiner

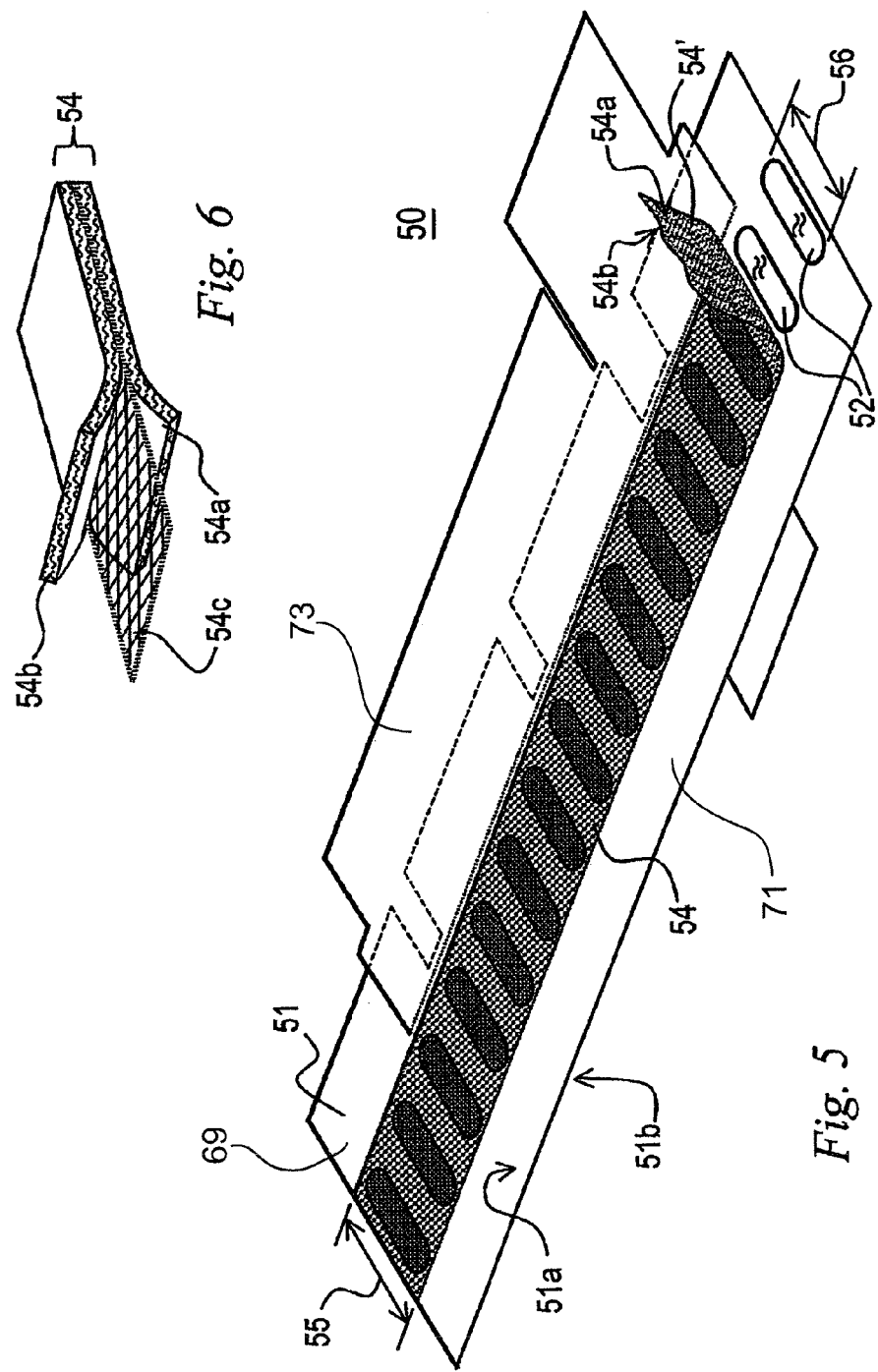

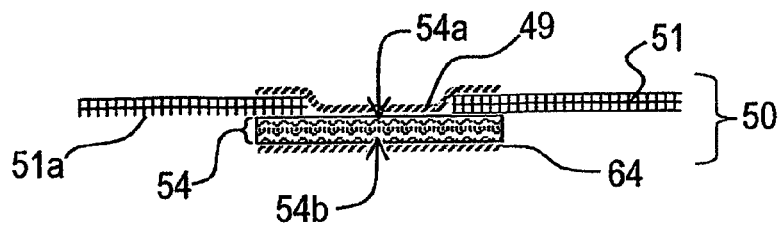
Fig. 9-a
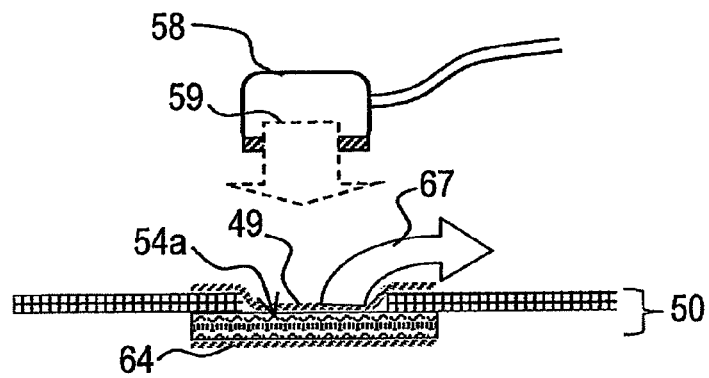
Fig. 9-b
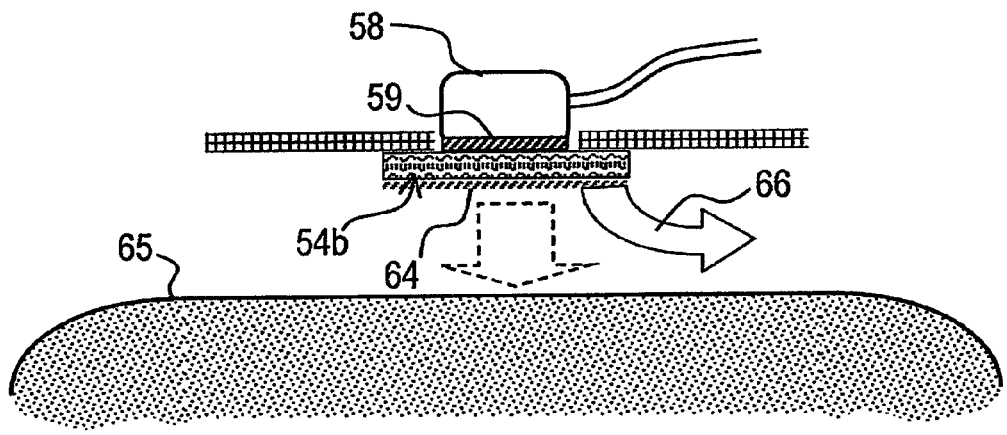
Fig. 9-c
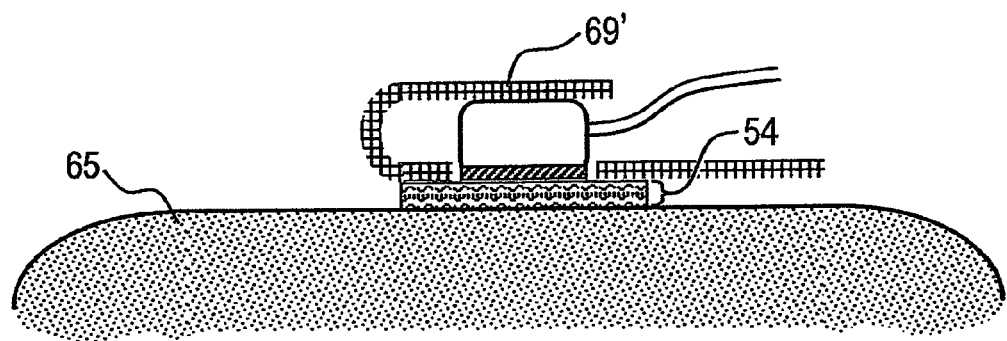
Fig. 9-d

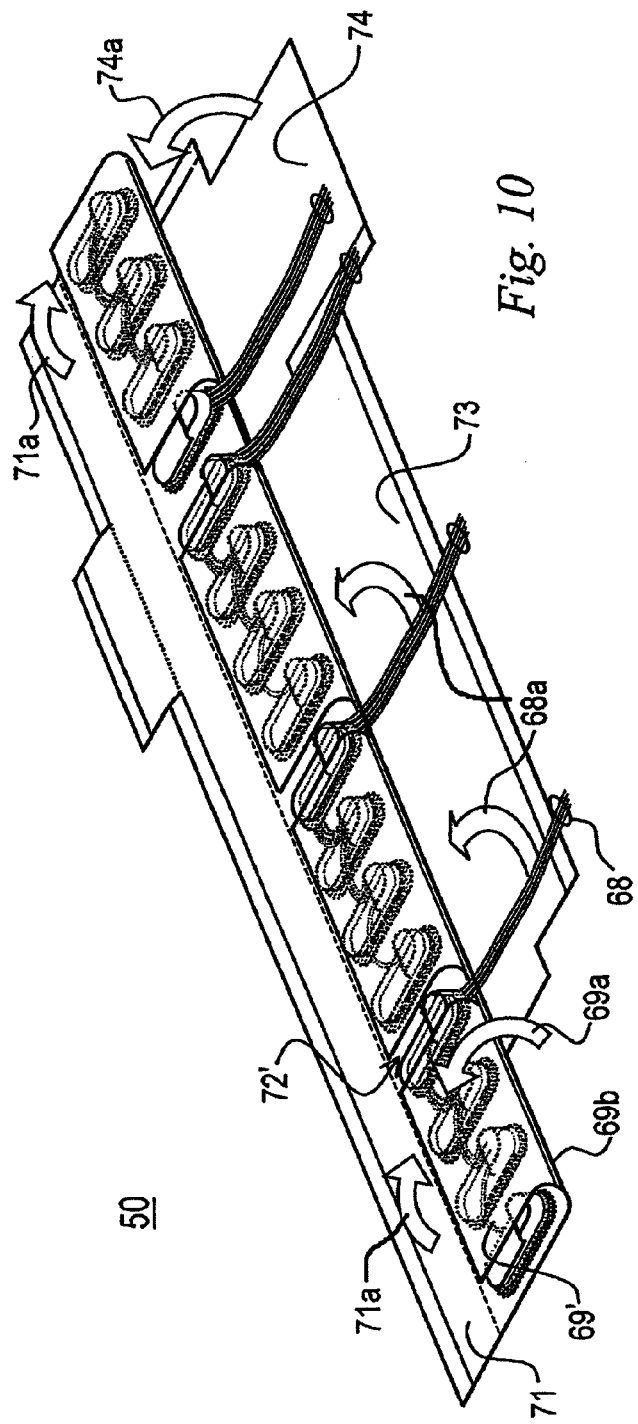
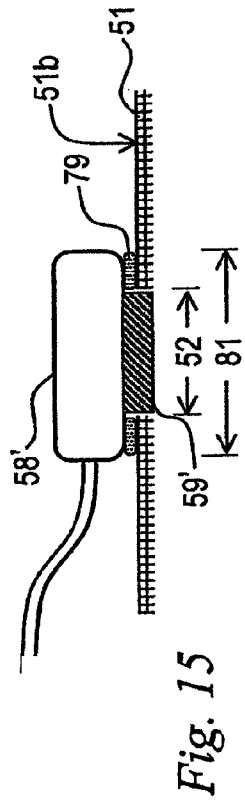
Fig. 10
Fig. 15

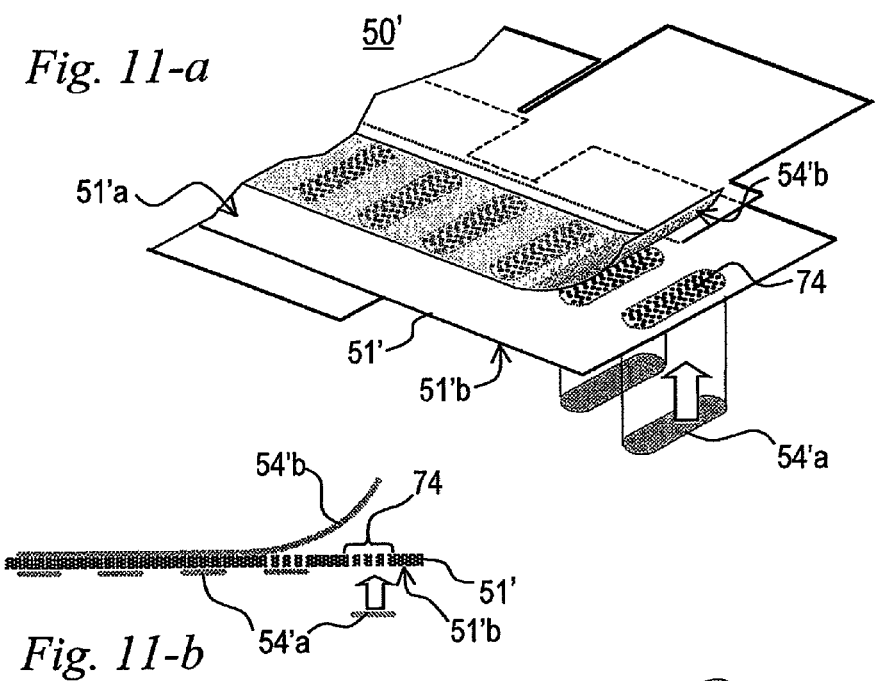
*Fig. 11-a*
*Fig. 11-b*
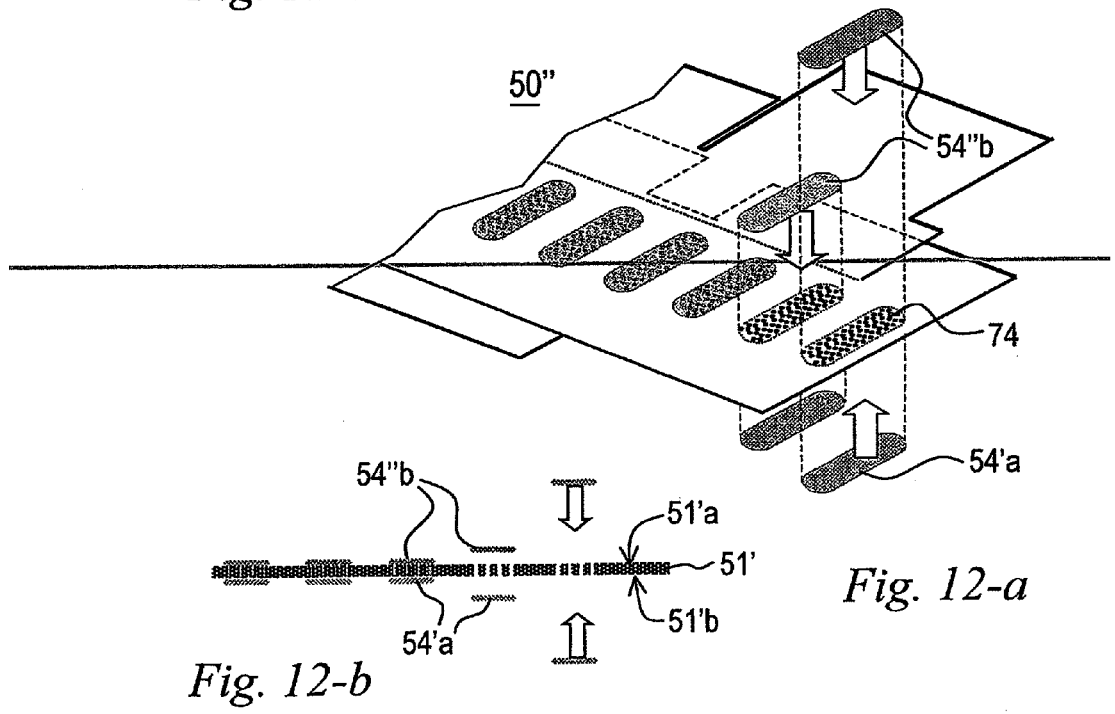
*Fig. 12-a*
*Fig. 12-b*

ELECTRODE SYSTEM FOR TRANSDERMAL CONDUCTION OF ELECTRICAL SIGNALS, AND A METHOD OF USE THEREOF

CROSS-REFERENCE TO RELATED APPLICATIONS

This application is a national phase entry under 35 U.S.C. §371 of International Patent Application PCT/BR2009/000414, filed Dec. 18, 2009, designating the United States of America and published in English as International Patent Publication WO 2010/069023 A2 on Jun. 24, 2010, which claims the benefit under Article 8 of the Patent Cooperation Treaty and under 35 U.S.C. §119(e) to Brazilian Patent Application Serial No. PI0805365-0, filed Dec. 19, 2008, the disclosure of each of which is hereby incorporated herein in its entirety by this reference.

FIELD OF THE INVENTION

The present invention relates to the electrodes used to apply transdermal electrical stimuli to patients and/or to detect electrical signals from patients, such as sets of electrodes used in electrical impedance tomography, however, without being limited to the latter.

DESCRIPTION OF THE PRIOR ART

The medical application of electrodes connected to specific equipment intended for electrical stimulation or detection of electrical signals comprehends both the application of currents or voltages through the skin, examples thereof comprising transcutaneous nerve or muscle stimulation and functional electrical stimulation, such as the detection of electrical signals exemplified by the electrocardiogram, the electroencephalogram, and the electromyiogram, as well as techniques whereby is applied an electrical signal through the skin, simultaneously measuring the resulting signals, as occurs with electrical impedance tomography.

The electrical impedance tomography—generally known by the acronym EIT: Electrical Impedance Tomography—is an already known technique which consists of placing a plurality of electrodes in contact with the skin of the patient on a given region, and performing a series of steps comprising the injection of a current between the electrodes of a pair of electrodes, measuring the electrical potentials of the remaining electrodes, and repeating this step for all the electrodes of the entire set of electrodes. The measured values are sent to data processing equipment and are subjected to a treatment, which results in an image showing the electrical impedance within the region of interest.

Contrary to other techniques used to follow up the conditions of the patient, the EIT is suitable for continuously monitoring the condition of the patient, due to being non-invasive and due to not involving risks that might limit the number and frequency of monitoring actions, such as occurs, for example, with X-rays.

Since the distance between the points on the skin whereto the electrodes are attached may vary, either due to the effects of the patient's breathing (in the case of thoracic or abdominal monitoring) or even due to movements from the part of the patient, it is necessary that the electrode supporting element, normally configured as a strap, be capable of following these movements, in order to warrant permanent contact between the electrodes and the skin. Patent Application No. BR PI0704408, of the same filing applicant of the instant application, illustrated in FIGS. 1 and 2 of the instant application, shows an electrode strap formed of a strip of fabric, both flexible and non-conductive, folded over itself in the longitudinal direction, resulting in a first section turned towards the patient and a second section oriented in the opposite direction, that is, externally to the patient. At spaced locations along the first section there is deposited a flexible conductive material, selectively in order to form a plurality of first circular or oblong regions or zones 34, intended to contact the skin of the patient. Each of these zones 34 has an extension 24 which extends towards the fold, surrounding the same and extending over the second section whereon it broadens forming a second zone 27, approximately coincident with the first zone. This second zone 27 serves to provide the electrical and mechanical connection to the points of contact 12 of a flexible, insulating and longitudinally non-deformable supporting strip 10, each point of contact 12 being connected, by means of a flexible conductive track 39 embedded in the supporting strip 10, to a connector 42 that is provided with means of contact with the cabling that connects the strap to the monitoring apparatus.

As may be observed in FIGS. 1 and 2, the structure in question is complex, which manufacture involves the performance of cutting/opening of windows 33 and intermediary spaces 37 between the first zones 34, as well as between the second zones 27 in the fabric material, in addition to the selective placement of the conductive material, the installation of the supporting strip 10, etc.

Moreover, the absence of shielding means of the flexible tracks 39 might entail the detection of interfering signals, thereby compromising the accuracy of the results. One other disadvantage of the object of the cited application resides in the act of there being required the manual application of a conductive gel material on the zones 34 in order to improve the electrical contact with the skin of the patient.

There are presently known in the art several alternatives for the preparation of electrodes that dispense the manual application of such gels. In this regard, in U.S. Pat. No. 5,785,040, entitled Medical Electrode System, there is disclosed a system comprising a flexible, non-conductive backing material, having juxtaposed to the face turned towards the patient a plurality of patches made of a conductive material which face a flexible non-conductive blade. The latter is provided with openings or windows in the positions corresponding to the pads, with dimensions slightly lesser than the same. Through such windows, each of these conductive patches contacts the upper side of a conductive gel plate, which lower face adheres to the skin of the patient. The conduction of electrical signals is provided by flexible cables whose ends are permanently secured to the faces of the conductive pads turned towards the flexible backing material. Due to this last characteristic, the assembly cannot be washed, which fact compromises the reuse thereof. It is an expensive solution in light of its complex structure, and its application is limited.

In U.S. Pat. No. 6,788,979, entitled Electrical Stimulation Compress Kit there is disclosed a system whereby a flexible insulating strap, equipped with a VELCRO®-type closure means, is applied by tightening around a part of the body of a patient, exerting a compressive force thereon. At certain points, this strap is crossed through by metallic terminals of a fastener type which outer pin provides a point for attachment for the terminal of the cable that conducts the electrical signals. The inner face of each terminal establishes an electrical contact with a conductive hook-loop fastener, which is removably attached to the strap by the adhesion of a first conductive gel layer. A second layer of conductive gel is in contact with the skin of the patient, the second layer being separated by a conductive web that may be made of metal or any other low resistivity material. This conductive web becomes necessary due to the small size of the area of the terminal turned towards the patient, which might result in a concentration of the transcutaneous current. The conductive web provides a uniform distribution of the current throughout the entire surface of the pad, reducing the contact resistance with the skin and avoiding the occurrence of current concentration points. In addition to the disadvantage represented by the need to use the pads, the described system has the disadvantage that the strap, in contact with the skin, is liable to become contaminated by sweat and other secretions; the washing or sterilization of the strap poses problems due to the presence of the metallic terminals and the VELCRO®-type adhesive means. The alternative, consisting in the mere disposal of the strap, constitutes a liability for the users of this system.

OBJECTS OF THE INVENTION

In view of what has been set forth above, one object of the present invention consists in the provision of a system of electrodes combining low cost and easy applicability to the patient.

One other object consists in the provision of a system of electrodes comprising low-cost elements, which disposal might not constitute an excessive burden to hinder the use thereof.

One further objective consists in the provision of a system that might dispense the use of conductive pads for uniform distribution of the current at the area of contact with the skin of the patient.

BRIEF SUMMARY

The objects set forth above, as well as others, are achieved by the invention by means of the provision of a system of electrodes formed of an assembly of electrode parts mechanically and electrically associated to the distal ends of the cables that conduct electrical signals to an equipment provided for the application of electrical stimuli or for the detection of electrical signals, such component parts being provided with an electrically conductive portion, and a low-cost portion comprising a support in the form of a flexible and porous blade, having applied to both faces thereof conductive portions formed by layers of electrically conductive materials, such layers being provided in electrical contact with one another, a first conductive portion, applied to the first side of the flexible and porous blade placed in contact with the electrode parts and a second conductive portion, applied to the second side of the blade placed in contact with the skin of the patient, the removable attachment of the electrode parts to the low-cost portion being provided by a first layer of adhesive material juxtaposed to the first side of the blade, and the removable attachment of the low-cost portion to the skin of the patient being provided by a second layer of adhesive material juxtaposed to the second face of the blade.

According to another characteristic of the invention, at least one of the layers of adhesive material forms portions that surround the conductive portions.

According to another characteristic of the invention, the electrically conductive material of at least one of the layers is simultaneously an adhesive material and a conductive material.

According to another characteristic of the invention, the blade is provided with means for positioning the electrode parts.

According to another characteristic of the invention, the positioning means are provided with visual indicators.

According to another characteristic of the invention, the positioning means are provided by mechanical means.

According to another characteristic of the invention, the positioning means are applied to the first side of the blade.

According to another characteristic of the invention, the low-cost portion comprises a support that consists of a strap or strip of flexible fabric (textile) material, having affixed onto at least one of the faces thereof a flexible strip, which the latter comprises a flexible and porous supporting blade coated on both faces thereof with layers of conductive and adhesive materials.

According to another characteristic of the invention, the flexible strip, comprising the layers of conductive and adhesive materials, is juxtaposed by means of adhesion of the first layer of adhesive material to the inner face of a strap of electrically insulating fabric/textile material.

According to another characteristic of the invention, the means for positioning the electrode parts are comprised by cutouts or openings in the strap of fabric/textile material through which the electrode parts are removably attached to the first layer of adhesive material of the strip.

According to another characteristic of the invention, the dimensions of the cutouts are slightly larger than those of the conductive parts of the electrode parts.

According to another characteristic of the invention, the means used for positioning the electrode parts comprise protuberant elements provided in correspondence with the outer side of the strap.

According to another characteristic of the invention, the means used for positioning the electrode parts comprise a template.

According to another characteristic of the invention, the simultaneously adhesive and conductive portions are constituted by at least one layer of solid gel.

According to another characteristic of the invention, the flexible strip consists in a continuous strip.

According to another characteristic of the invention, the flexible strip is interrupted between the cutouts, the dimensions of the pieces of the conductive strip being sufficient to occlude the cutouts in the strap.

According to another characteristic of the invention, the electrical contact between the upper layers of conductive materials is provided by means of pores provided in the supporting blade of the strip.

According to another characteristic of the invention, the layers of electrically conductive materials and adhesive materials are applied directly over the fabric/textile material strap.

According to another characteristic of the invention, the electrical contact between the layers of conductive materials is provided by means of pores provided in the fabric/textile material strap.

According to another characteristic of the invention, the materials of the layers comprise a solid gel that is simultaneously conductive and adhesive.

According to another characteristic of the invention, at least one of the solid gel layers is applied in a selective manner.

According to another characteristic of the invention, the areas of mechanical fastening and electrical contact of the electrode parts are provided by the first solid conductive and adhesive gel layer applied selectively on the outer side of the strap.

According to another characteristic of the invention, the means for electrical contact and removable mechanical attachment to the skin of the patient are provided by the second layer of solid conductive and adhesive gel applied selectively on the inner side of the strap.

According to another characteristic of the invention, both layers of solid gel are selectively applied in the form of portions with defined dimensions and spacing distances, each of the portions on the outer side, forming the area of mechanical fastening and electrical contact of the electrode parts, in substantial alignment with the portion applied on the inner side of the strap.

According to another characteristic of the invention, the electrode parts are secured, in a semi-permanent manner, to the first layer by means of juxtaposition and slight pressure.

According to another characteristic of the invention, the electrode parts comprise, individually, a conductive portion in the form of a conductive blade and a physical and electrical connection thereof with an electrical signal conduction cable, the conductive portion having a shape and size compatible with the openings through which there is provided the contact of the conductive portion with the first conductive layer.

According to another characteristic of the invention, the strap is provided with means for positioning the electrode parts.

According to another characteristic of the invention, the positioning means comprise the openings provided in the strap.

According to another characteristic of the invention, the positioning means are provided by a slab of low density flexible insulating material, such as rubber foam or synthetic resin, applied on the outer side of the strap, provided with openings that are coincident with the areas intended for mechanical fastening and electrical contact of the electrode parts. According to another characteristic of the invention, the slab is substantially continuous.

According to another characteristic of the invention, the slab is segmented, being comprised of segments distanced from one another in the longitudinal and transversal directions of the strap According to another characteristic of the invention, the strap is provided, along the longitudinal borders thereof, of flaps that are superimposed by folding on the region of the strap wherein are provided the electrodes, providing a measure of protection thereto as well as to the cables associated therewith.

BRIEF DESCRIPTION OF THE DRAWINGS

Further characteristics and advantages of the present invention will be better understood by means of the description of exemplary and non-limitative embodiments thereof, and of the figures to which such embodiments refer, wherein:

FIG. 5 shows, by means of a perspective view of an inner side, which remains in contact with a patient, a strap structured in accordance with the principles of the present invention.

FIG. 6 shows, by means of a perspective view, a strip coated on both sides with materials that are simultaneously conductive and adhesive, which may be used together with the strap of the exemplary embodiment of FIG. 5.

FIG. 9-a through 9-d show, by means of cross-sectional schematic views, the various stages of the sequence of application of the strap to the patient.

FIG. 10 depicts the folding of the outer flaps of protection of the electrode parts and respective cables.

FIG. 11-a and 11-b depict an additional embodiment of the invention.

FIG. 12-a and 12-b show a variation of the additional embodiment depicted in the preceding figures.

FIG. 15 illustrates another form of an embodiment of the invention.

DETAILED DESCRIPTION OF THE INVENTION

Figure 1:
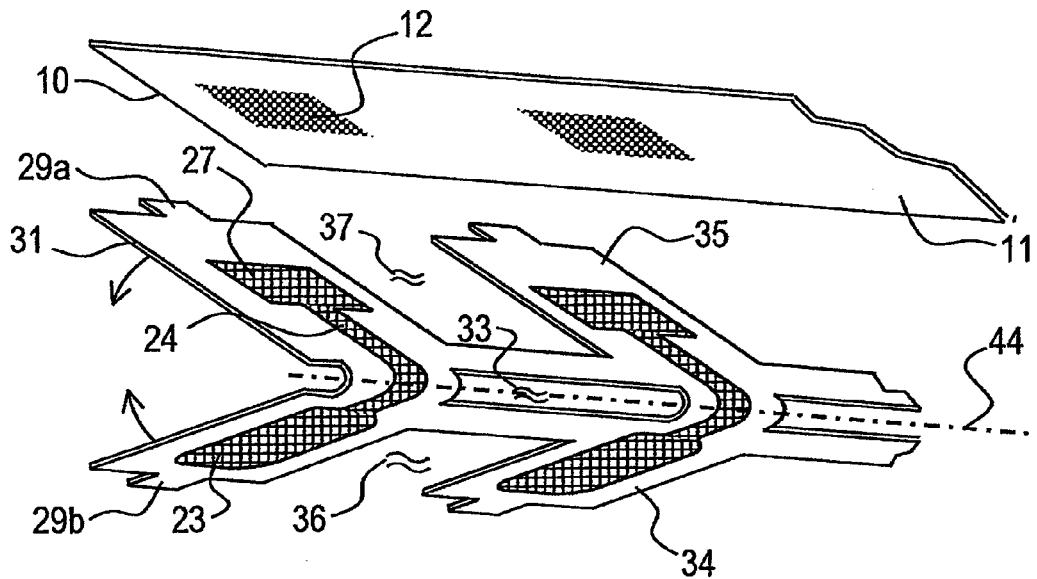
FIGS. 1 and 2 depict an electrode strap (belt) structured in accordance with the prior art, as described in Patent Application No. BR PI 0704408, filed by the same applicant of the instant application.
Figure 2:
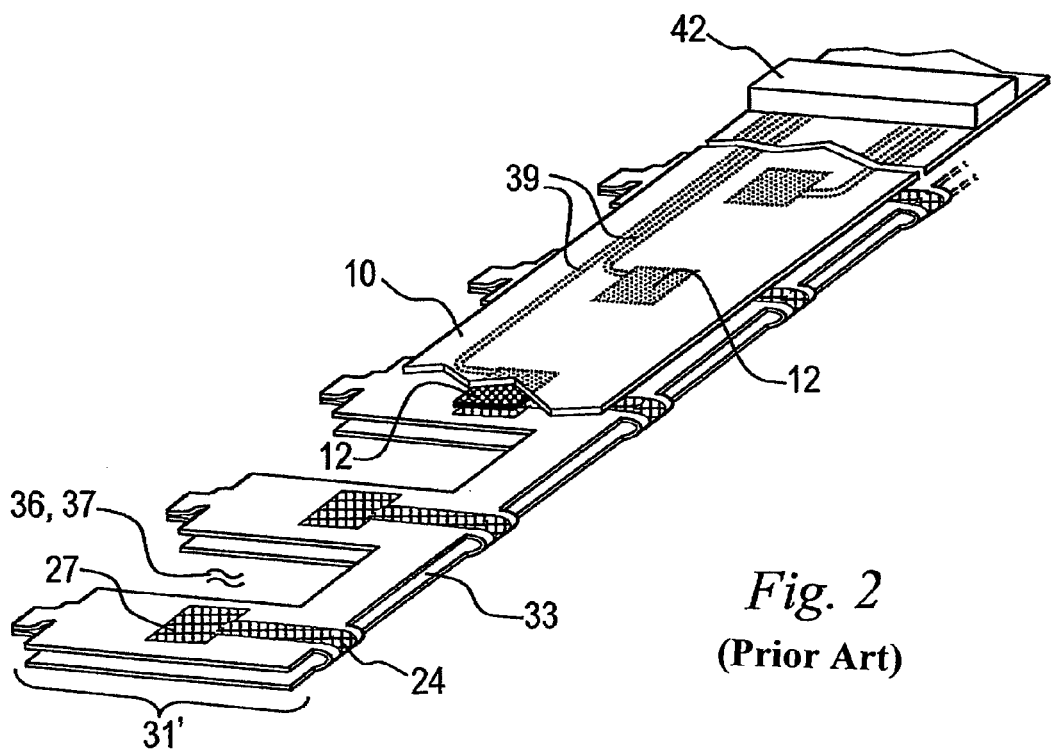
Figure 3:
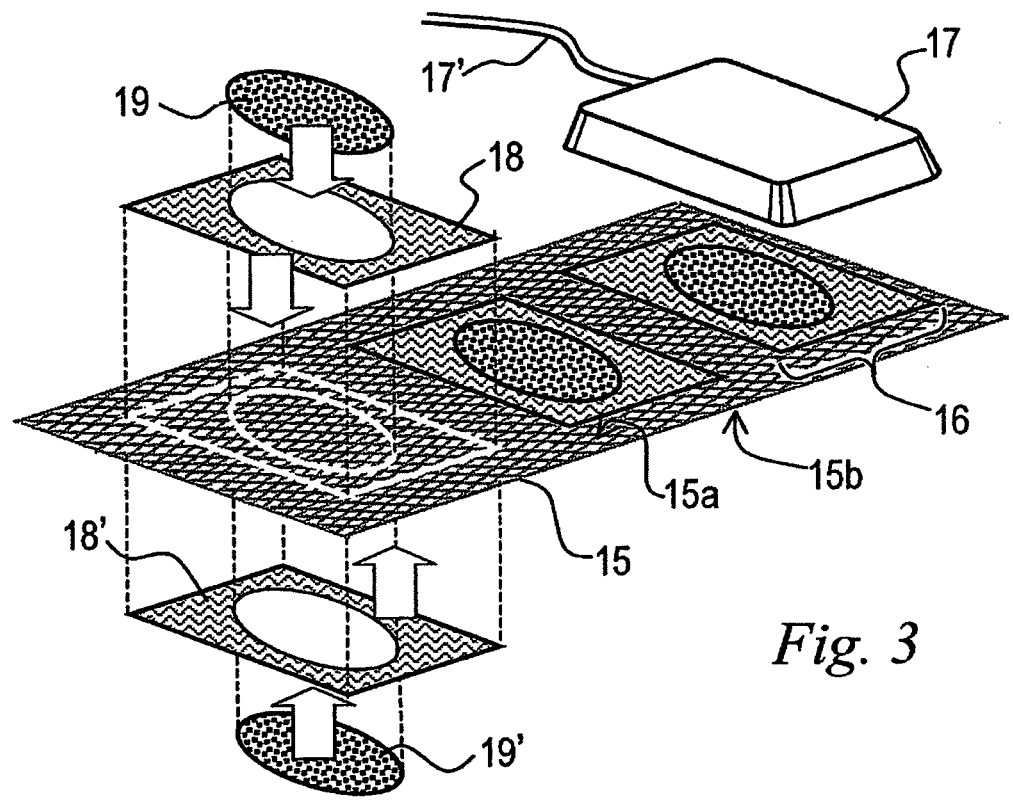
FIG. 3 shows a first embodiment of the inventive concept, using a flexible supporting strip, having applied on both sides thereof portions of conductive and adhesive materials.

FIG. 3 shows a first embodiment 30 of the invention, comprising a flexible strip 15, preferably made of fabric/textile material, coated with conductive parts with defined size and spacing on portions 19 and 19', respectively applied on the first side 15a and on the second side 15b thereof, the electrical contact between the conductive portions being provided by means of the material of the flexible strip 15, either by means of the porous texture thereof, or by means of pores opened by known means, such as by mechanical perforation (not illustrated in the figure). According to the principles of the invention the conductive materials of portions 19 and 19' comprise solid gels. As shown in the figure, the portions 19 and 19' are substantially aligned with one another, that is, they occupy substantially coincident positions on the opposite sides of the flexible strip 15. Surrounding the portions 19 and 19', there are provided regions 18 and 18' of adhesive material, respectively applied on the first and second sides 15 a, 15b of the flexible strip 15. This material, which may consist in a solid gel, provides the retention of the electrode parts 17 on the surface of the flexible strip 15 and the contact of those parts with the conductive material of portion 19, enabling the transmission to the latter of the electrical signals that travel along the connecting cables 17'. Due to the fact that the portions 19 and 19' are in mutual electrical contact, and the latter is in contact with the skin of the patient, the arrangement shown in FIG. 3 effectively provides the transmission of electrical signals between the skin of the patient (not illustrated) and the connecting cable 17'. According to what is shown in FIG. 3, the dimensions of contact area 16, formed by the conductive portions 19, 19'and adhesive regions 18, 18', correspond substantially to the dimensions of the lower part (not visible in the figure) of the electrode part 17, the lower part comprising an electrically conductive area.

Figure 4:
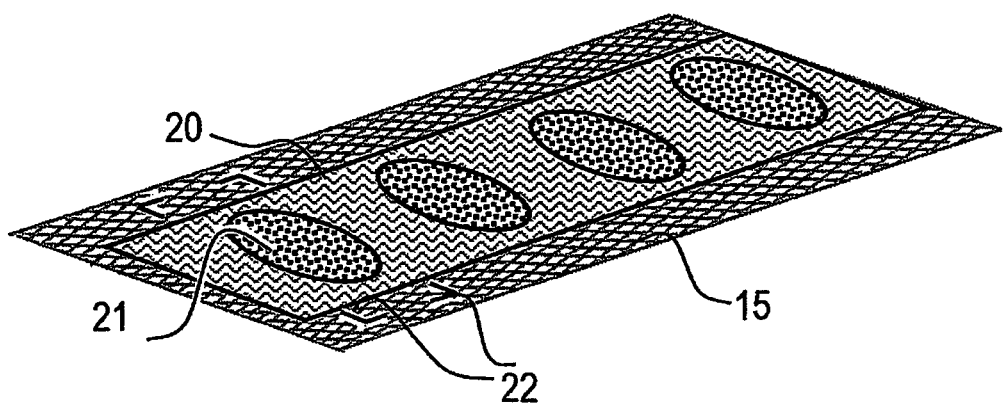
FIG. 4 shows a second embodiment of the inventive concept, wherein the adhesive material is applied in the form of a continuous layer.

FIG. 4 illustrates a variation 40 of the arrangement shown in FIG. 3, differing therefrom in that an adhesive gel layer 20 is applied in a continuous manner, this gel providing the means for removable retention of the electrode parts (not shown) and physical contact thereof with conductive gel portions 21. The accurate positioning of the electrode parts may be aided by the provisions of positioning means, which in FIG. 4 are indicative signs 22 that are preferably printed on the surface of the flexible strip 15.

Notwithstanding that FIGS. 3 and 4 exemplify strips, wherein are employed conductive materials distinct from the adhesive materials, there may be used, in the invention, materials that simultaneously exhibit adhesive properties and conductive properties, such materials being known and available in the form of solid gel. Furthermore, the composition of the gel that is applied to the first side of the flexible strip 15 may be the same or different from that which is applied to the second side, since the latter is supposed to establish the contact with the skin of the patient, while the other is intended to contact the electrode parts.

FIG. 5 illustrates a non-restrictive exemplary embodiment 50 of the invention, whereto were added elements that complement the functionalities provided by the exemplary embodiments of FIGS. 3 and 4. The embodiment 50 comprises a strap of flexible non-conductive material 51, which inner surface 51a is intended to be placed in contact with the skin when applied to the patient, with the opposite side 51b being provided facing outwards to allow the installation of the electrode parts. As illustrated in FIG. 5, the flexible strap 51 is provided with a plurality of cutouts with the shape of oblong openings spaced along a region that extends substantially along the center thereof.

According to the principles of the invention and as illustrated in FIG. 5, a flexible strip 54 structured in accordance with the principles exemplified in the embodiments of FIGS. 3 and 4 is glued on the region occupied by the openings, a width 55 thereof being sufficient to obstruct entirely the openings. In practice, the width 55 is slightly larger than dimension 56 of the openings in the transversal direction of the flexible strap 51, in order to ensure the full occlusion thereof. The flexible strip 54 is permanently bound to the inner side 51a of the flexible strap 51, and it should be noted that the raising of one of the ends 54' thereof as illustrated in FIG. 5 constitutes a mere graphical resource intended to enhance openings 52 and render the same more visible to the viewer hereof.

FIG. 6 illustrates the flexible strip 54, by means of a view in perspective wherein the vertical dimension—the thickness—is considerably enlarged in order to evidence the elements that compose the same. As may be observed, the strip comprises a central element or supporting blade 54c intercalated between a first layer of adhesive and conductive gel 54a and a second layer of adhesive and conductive gel 54b. The central element 54c may be constituted by a screen which mesh size is substantially open, in order to allow, through the openings therethrough, the contact and mutual adhesion between the first and second adhesive and conductive gel layers 54a, 54b, that are electrically conductive, wherein there may be used a non-woven screen in a preferred embodiment of the invention. The characteristics of the adhesive and conductive gel layers 54a, 54b may be the same or may be mutually distinct, in light of their different functions. The adhesive and conductive gel layer 54a, which stays adhered to the flexible strap 51, (FIG. 5), should further allow the adhesion and removal of the electrode parts, as will be seen in the following. On the other hand, the adhesive and conductive gel layer 54b (FIG. 5) should allow the attachment and removal of the flexible strap 51 to/from the skin of the patient, and should thereby exhibit characteristics compatible therewith, without causing irritation or allergic reactions.

Figure 7:
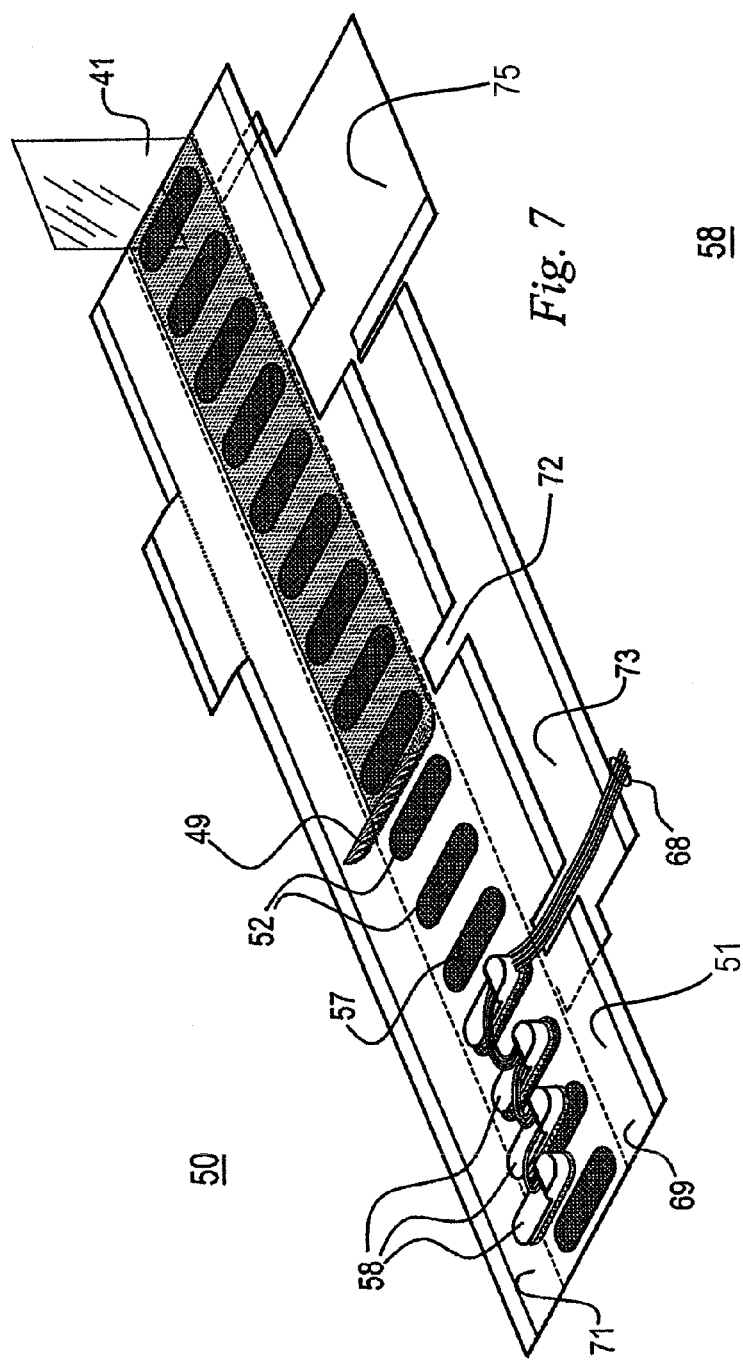
FIG. 7 shows a perspective view of the outer face of the strap shown in FIG. 5, structured in accordance with the principles of the present invention.

FIG. 7 shows the same flexible strap 51, observed on its outer side, which side will stay exposed upon the application thereof to the patient. As may be seen in the FIG. 7, in this position the openings 52 allow selective access to the contact areas 57 of the conductive and adhesive and conductive gel layer 54a of the flexible strip 54 (FIGS. 5 and 6), such cutouts 52 serving as means for positioning and spacing the electrode parts 58. For the assembly of the latter it will suffice to remove the protective film 49 and juxtapose, applying thereby a slight pressure, the electrode parts 58 against the contact areas 57.

Still in accordance with FIG. 7, in a preferred embodiment of the invention, there are provided, parallel to a longitudinal axis 41 of the flexible strap 51, flaps 69, 71, 73 and 75 intended to protect, by folding, the electrode parts 58 and respective cable assemblies 68 upon the assembly thereof on the flexible strap 51. The flaps 69, 71, 73, 75 may be provided with retention means upon the folding, such as adhesive bands along the outer borders thereof or VELCRO®-type or equivalent closure means. However, these flaps 69, 71, 73, 75 may not be present in other embodiments.

Figure 8:
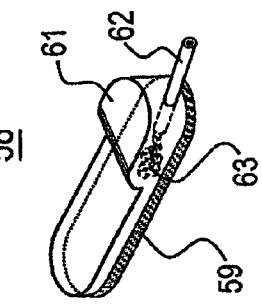
FIG. 8 shows, by means of a perspective view, an electrode part used in connection with the present invention.

According to the detail shown in FIG. 8, each electrode part comprises on the lower side thereof a conductive portion 59, which may comprise a metal plate—for example, made of copper, stainless steel, or an equivalent metal—or made of a conductive plastic material. Internally to the body of the part, preferably made of an insulating plastic, there is provided the union, preferably by welding 63, of an end of a cable 62 for carrying electrical signals between the patient and the monitoring equipment, for example, an EIT apparatus. As illustrated in the figure, the dimensions of the opening 52 are provided to accommodate, with a minimal spacing gap, the conductive portions 59 of the electrode parts 58.

FIG. 9-a through 9-d illustrate a preferred method of application of the flexible strap 51 to the patient, by means of a sequence of simplified sectional views corresponding to a cross-sectional plane 41 indicated in FIG. 7. The initial condition of the embodiment 50 is shown in FIG. 9-a, wherein there may be observed that the conductive and adhesive gel sides 54a, 54b of the flexible strip 54 are protected by disposable films: the protective film 64 protects the conductive and adhesive gel side 54b oriented towards the patient and the protective film 49 protects the conductive and adhesive gel side 54a oriented towards the flexible strap 51 and accessible from the outside through the openings 52 (not referenced in this figure).

The first step of the application method, illustrated in FIG. 9-b, consists in the removal of the protective film 49, represented by the arrow 67, thereby exposing the conductive and adhesive gel side 54a that forms the areas of contact with the electrode parts 58 (these areas of contact are referred with the numeral 57 in FIG. 7), in addition to becoming adhered to the inner side 51a of the flexible strap 51. To each of these exposed contact areas there is juxtaposed an electrode part 58, which adhesion is provided by the simple compression of the conductive side 59 against the surface of the conductive and adhesive gel 54a, 54b.

Subsequently, the electrode parts 58 and their respective cables are protected by folding over the same side flaps of the strap, if such flaps are present, as illustrated in FIG. 10. FIG. 10 illustrates the strap upon the first flap 69 (FIG. 5) having been folded to the position 69', becoming superimposed over the electrode parts 58, there being noted that cable assemblies 68, each of the same corresponding to a set of four electrode parts 58, extend to the outside through the cutouts 72'. After this first folding, the flap 71 is folded in the direction indicated by the arrow 71a, becoming superimposed over the already folded flap 69'. Subsequently, the cable assemblies 68 are deviated as indicated by arrows 68a, in order to be juxtaposed to the border 69b of the folded flap 69', and are brought together forming a set of cable assemblies 68, which protuberates through the cutout present between the flaps 73 and 74. Finally, these last flaps 73, 74 are folded, as indicated by the arrows 69a and 74a.

Subsequently, an assembly formed by a strap carrying electrodes is applied to a patient. To that end, the protective film 64 of the conductive and adhesive and conductive gel layer 54b is removed, as indicated by the arrow 66 in FIG. 9-c. The assembly is then pressed against the skin of a patient 65, as illustrated in FIG. 9-d, whereby the retention thereof is provided by the adhesive and conductive gel layer 54b, which also intermediates the carrying of the electrical signals. In FIG. 9-d the protective flap 69' is superimposed over the electrode part 58. For better clarity of the figure, the remaining protective flaps have been omitted in the drawing.

As illustrated in FIG. 5, the flexible strip 54 is provided in the form of a single piece, without interruptions between the adjacent openings 52. Notwithstanding the fact that the continuity of the flexible strip 54 provides a resistive path between the adjacent electrode parts in contact with the skin of the patient, the effect of such continuity is negligible, and does not substantially influence the electrical behavior of the assembly. Thus, for example, considering the typical values of 4 cm$^2$ of a contact area 57 (FIG. 7) for each electrode, a distance of 1.5 cm between the borders of adjacent electrodes, a thickness of 0.3 mm for the conductive gel layer and a gel resistivity p=1000 ohm-cm, there are obtained as a result the approximate values of from 10 to 20 kΩ between adjacent electrodes, while the resistance between the electrode part and the skin of the patient is of the order of only 5 to 10 Ω.

However, the inventive concept disclosed herein also includes an assembly in which the flexible strip 54 is segmented, that is, having interruptions between adjacent electrodes, with the segments having dimensions that are slightly larger, both in length and in width, than the openings 52, in order to fully occlude the latter.

In an additional embodiment 50' of the disclosed concept, the flexible strip 54 is not used, and the adhesive and conductive gel layers 54a and 54b are deposited directly on the opposite sides of the flexible strap 51. A first variant of that embodiment is shown in FIGS. 11-a and 11-b, of which the first shows a part of a strap 51' seen in its inner side 51'a, that is, which will be in contact with the patient, and the second is a cross-sectional view with the vertical dimension having been enlarged. As illustrated, in this embodiment there have been omitted the cutouts or openings 52 of the preceding embodiment 50. In the areas 74 corresponding to the positions of the electrodes there are practiced a plurality of small through-openings or pores that provide communication between the outer side 51'b and the inner side 51'a of the strap 51'. Such openings 52 may be obtained by mechanical means or by any other known means of perforation, and this communication may further be provided by the web, itself, of the strap 51', provided that the same is sufficiently porous.

Upon the provision of the porous areas 74, there are applied on opposite sides the conductive gel layers, to wit, the internal layer, which is continuous, of the gel 54'b on the inner side 51'a of the strap 51' and the outer layer of the gel 54'a, which is segmented, on the outer side 51'b of the strap 51', such gels being equivalent to the adhesive and conductive gel layers 54b and 54a, respectively, of the embodiment illustrated in FIGS. 5 and 6. This application may be provided using any known process, such as by spraying, silk-screen printing, offset printing, etc., provided that there is maintained the alignment between the areas coated with adhesive and conductive gel and the porous areas 74, whose pores enable the physical and electrical contact between the inner and outer layers.

In FIGS. 12-a and 12-b there is illustrated a constructive variation of the preceding embodiment 50", which differs from this latter only in regard of the inner layer of adhesive and conductive gel, which is deposited in segments 54"b, using the already cited application processes. It should be noted that, in this case, there should exist an alignment between the internal gel portions 54'b, the external gel portions 54'a and the areas 74, that is, these elements should be provided substantially coincident with one another. In a preferred embodiment of the invention, the dimensions of the segments 54"b and portions 54'a are substantially coincident with those of the conductive portions 59 of the electrode parts 58.

Figure 13:
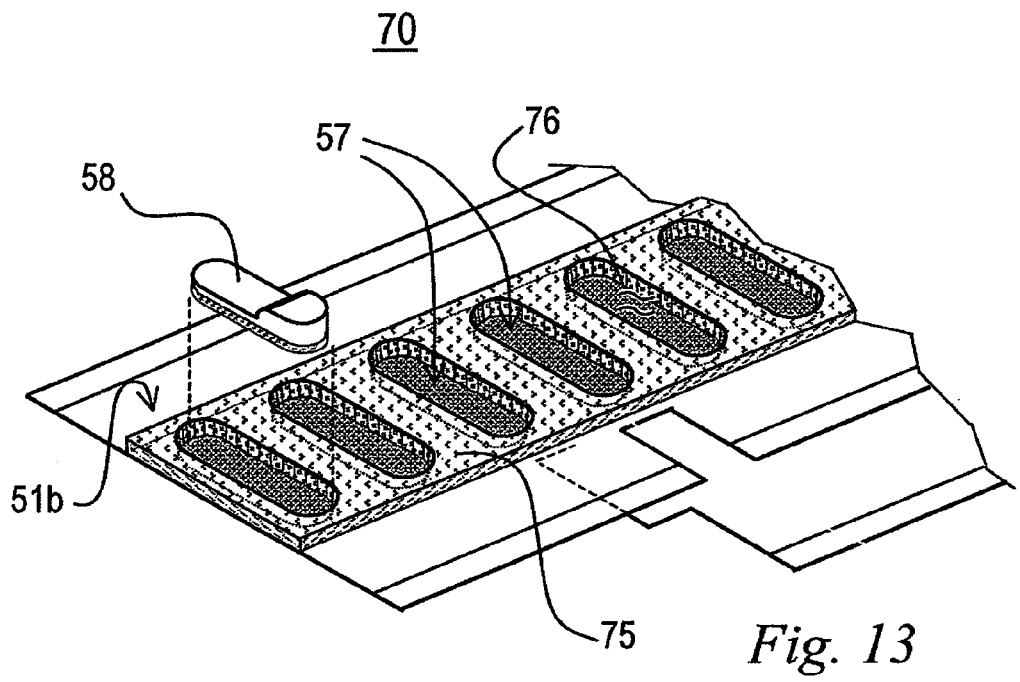
FIG. 13 shows an implementation of the mechanical positioning means of the electrode parts on the strap according to the present invention.

As mentioned in connection with FIGS. 5 and 7, the means for positioning the electrode parts 58 may be provided by the openings 52, as indicated in those figures. However, there may be used other positioning means, such as printed insignia, elements in relief glued on the outer surface of the strap 51', or equivalent elements. In FIG. 13 there is illustrated the use of a slab of soft elastic material 75, such as rubber foam, a plastic material or an equivalent material, extending along the region occupied by the electrode parts 58. This slab 75 is provided with openings or windows forming holes or frames 76 having dimensions compatible with those of the contact areas 57 that remain exposed at the bottom of the holes 76, over which are applied the electrode parts 58.

Figure 14:
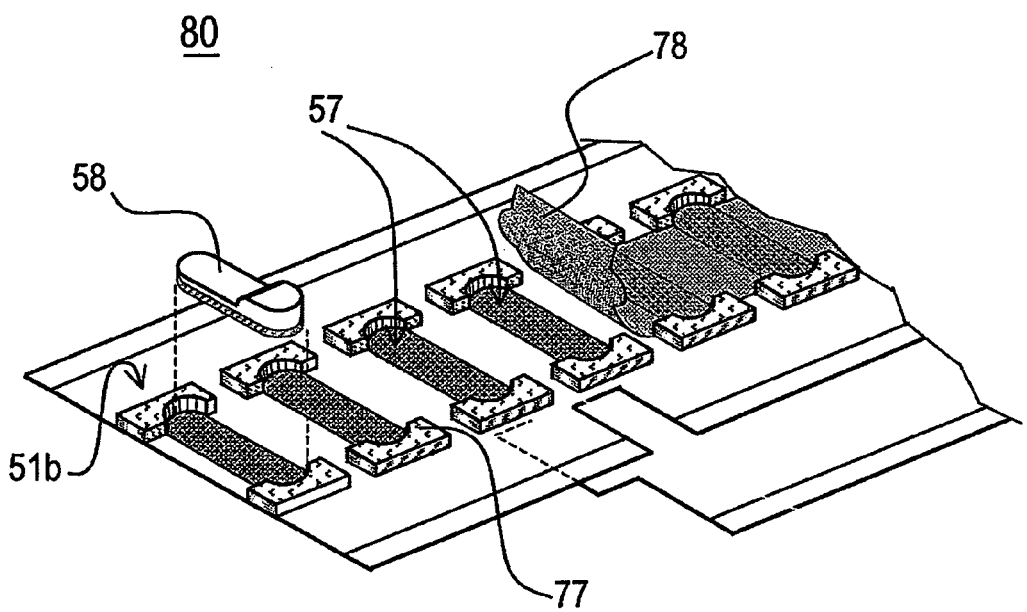
FIG. 14 illustrates an additional form of implementation of the means for positioning the electrode parts on the strap according to the present invention.

In order to provide an enhanced flexibility to the assembly, the positioning slab 75 described in connection with FIG. 13 may be segmented, as indicated in FIG. 14. In this figure, positioning elements 77 are mutually distanced both in the lengthwise direction and across the width of strap 80. This transversal distancing allows the use of a protective film 78, which covers the exposed contact areas 57 during the storage of the strap 80, and is removed at the time of use thereof.

Although the invention has been described with reference to specific exemplary embodiments, it should be understood that there may be introduced modifications therein by technicians skilled in the art, without deviation from the scope of the basic inventive concept thereof.

In an additional form of an embodiment of the invention, the electrode parts are positioned separately with relation to the strap 51, by means of use of an auxiliary template, not illustrated in the figures, whereon these electrode parts are mounted. After this mounting, the template carrying the electrode parts is applied to the flexible strap 51, the parts then remaining attached by adhesion to the strap 51, which is subsequently applied to the patient. Optionally, the strap 51 will not be used, and the template with the electrode parts 58 may be applied directly on the flexible strip 54 having been previously applied on the skin of the patient, in which case the protection of the electrode parts 58 and their respective cables may be provided by the template itself, or eventually by a protective band (not illustrated) placed externally. In another alternative form of an embodiment of the invention, the template is constituted by the flexible strap 51 per se without the flexible strip 54. This embodiment is shown in FIG. 15, wherein the border of each opening 52 is coated, on the outer side 51b of the flexible strap 51, by adhesive strips 79. The assembly of the electrode parts 58' shall be provided by superimposing the borders thereof onto the adhesive strips 79, as indicated in FIG. 15, and it should be noted that in this case at least one of dimensions 81 of the electrode part 58' shall correspond to the sum of the dimension of the opening 52 and the width of the adhesive strips 79. Upon mounting the electrode parts 58', according to the illustration of FIG. 15, the flaps are folded as described in connection with FIG. 10. At the time of use, the flexible strip 54 is applied to the skin of the patient, thereupon superimposing over this flexible strip 54, the assembly formed by the strap 51 carrying the electrode parts 58'.

Therefore, the present invention is defined and delimited by the set of claims that follow.

The invention claimed is:

1. A system of electrodes for transdermal conduction of electrical signals, the system comprising:
   a flexible strap having an inner surface for being placed in contact with a patient and an outer surface for facing outward from the patient, wherein the flexible strap includes a plurality of apertures linearly spaced along a region of the flexible strap, each aperture of the plurality of apertures extending from the outer surface of the flexible strap to the inner surface of the flexible strap, the flexible strap further comprising:
      at least one first foldable flap extending from a first longitudinal side of the flexible strap; and
      at least one second foldable flap extending from a second longitudinal side of the flexible strap, opposite the first longitudinal side;
   a flexible strip including an electrically conductive and adhesive material, the flexible strip having a first side adhered to the inner surface of the flexible strap along a region having the plurality of apertures, and a second side configured for removable attachment to a patient; and
   a plurality of electrode parts removably coupled to the first side of the flexible strip through the plurality of apertures of the flexible strap, each electrode part of the plurality of electrode parts comprising:
      a face establishing electrical contact, by juxtaposition, with the electrically conductive and adhesive material of the flexible strip to provide electrical contact between the patient and the electrode part through the electrically conductive and adhesive material of the flexible strip; and
      a portion extending from the face and out of a respective aperture of the plurality of apertures, the portion being associated with a distal end of an electrical conduction cable configured to carry an electrical signal to at least one equipment configured for application of electrical stimuli or detection of electrical signals.

2. The system of electrodes of claim 1, wherein the electrically conductive and adhesive material include portions with defined dimensions and locations.

3. The system of electrodes of claim 2, wherein the portions have dimensions that substantially correspond to the dimensions of conductive portions of the plurality of electrode parts juxtaposed thereto.

4. The system of electrodes of claim 1, wherein the electrically conductive and adhesive material comprises a solid gel.

5. The system of electrodes of claim 1, wherein the electrical conduction cables associated with each electrode part of the plurality of electrode parts are grouped in cable bundles.

6. The system of electrodes of claim 1, wherein the at least one second foldable flap of the flexible strap further comprises a plurality of foldable flaps having cutouts between adjacent foldable flaps of the plurality of foldable flaps, the cutouts between adjacent foldable flaps having at least one electrical conduction cable extending therethrough.

7. The system of electrodes of claim 1, wherein the electrically conductive and adhesive material comprises individual segments.

8. The system of electrodes of claim 1, further comprising positioning elements configured for positioning the plurality of electrode parts.

9. The system of electrodes of claim 8, wherein the positioning elements include visual indication signals or insignia.

10. The system of electrodes of claim 8, wherein the positioning elements include mechanical elements.

11. The system of electrodes of claim 10, wherein the positioning elements comprise elements in high-relief juxtaposed to the outer surface of the flexible strap.

12. The system of electrodes of claim 11, wherein the positioning elements comprise a slab of soft material extending along the region occupied by the plurality of electrode parts, provided with openings that leave uncovered areas of contact of the plurality of electrode parts.

13. The system of electrodes of claim 11, wherein the positioning elements comprise a segmented slab defining a plurality of positioning elements mutually spaced apart from one another both in the lengthwise direction and across a width of the flexible strap.

14. The system of electrodes of claim 8, wherein the positioning elements comprise an auxiliary template carrying the plurality of electrode parts are mounted, and wherein the auxiliary template carrying the electrode parts is applied to the flexible strap.

15. The system of electrodes of claim 14, wherein a border of each aperture of the plurality of apertures of the flexible strap is provided with at least one adhesive strip, each electrode part of the plurality of electrode parts having at least one of its dimensions equivalent to a sum of the dimension of a respective aperture of the plurality of apertures and a width of a respective at least one adhesive strip.

16. An apparatus, comprising:
   a flexible strap having an inner surface, an outer surface and a plurality of apertures extending from the outer surface and the inner surface, the flexible strap further comprising:
      at least one first foldable flap extending from a first longitudinal side of the flexible strap; and
      at least one second foldable flap extending from a second longitudinal side of the flexible strap, opposite the first longitudinal side;
   a flexible strip including an electrically conductive and adhesive material having a first side and a second side, the first side adhered to the flexible strap, and the second side configured for attachment to a patient; and
   a plurality of electrode parts removably disposed on the first side of the electrically conductive and adhesive material of the flexible strip and extending from the first side of the electrically conductive and adhesive material through the plurality of apertures and at least partially out of the plurality of apertures.

17. The apparatus of claim 16, wherein the electrically conductive and adhesive material includes a first layer and a second layer having a central supporting element made of a porous flexible material therebetween.

18. The apparatus of claim 17, wherein the porous flexible material has openings selected from the group consisting of pores, perforations, and openings of a mesh structure.

19. The apparatus of claim 16, wherein the flexible strap includes a fabric material.

20. The apparatus of claim 16, wherein the flexible strap further includes a positioning element configured to position the plurality of electrode parts at least substantially in alignment with the electrically conductive and adhesive material through the plurality of apertures.

21. The apparatus of claim 20, wherein the positioning element is selected from the group consisting of a visual indicator printed on the flexible strap, a mechanical element, a template, a protuberant element, and a positioning slab.

22. The apparatus of claim 16, further comprising a monitoring equipment operably coupled to the plurality of electrode parts to receive electrical signals from the plurality of electrode parts.

23. The apparatus of claim 22, wherein the monitoring equipment includes an electric impedance tomography apparatus.

24. The apparatus of claim 16, wherein the at least one first foldable flap comprises a plurality of foldable flaps having cutouts between adjacent foldable flaps of the plurality of foldable flaps.

25. The apparatus of claim 24, wherein each foldable flap of the plurality of foldable flaps has a different longitudinal length and extends a different length from the first longitudinal side of the flexible strap in comparison to another foldable flap of the plurality of foldable flaps.

26. The apparatus of claim 16, wherein the at least one second foldable flap comprises a plurality of portions, wherein each portion of the plurality of portions of the at least one second foldable flap has a different longitudinal length and extends a different length from the second longitudinal length of the flexible strap in comparison to another portion of the plurality of portions of the at least one second foldable flap.

27. The apparatus of claim 16, wherein the flexible strap further comprises at least one third foldable flap extending from the first longitudinal side such that the at least one third foldable flap is foldable over the at least one first foldable flap.

\* \* \* \* \*

UNITED STATES PATENT AND TRADEMARK OFFICE
CERTIFICATE OF CORRECTION

PATENT NO. : 9,220,431 B2
APPLICATION NO. : 13/132300
DATED : December 29, 2015
INVENTOR(S) : Albert Holzhacker It is certified that error appears in the above-identified patent and that said Letters Patent is hereby corrected as shown below:

In the specification:

| | | |
|---|---|---|
| COLUMN 1, | LINE 15, | change "P10805365-0," to --PI0805365-0,-- |
| COLUMN 6, | LINE 8, | change "FIG. 9-*a*" to --FIGS. 9-*a*-- |
| COLUMN 6, | LINE 13, | change "FIG. 11-*a*" to --FIGS. 11-*a*-- |
| COLUMN 6, | LINE 15, | change "FIG. 12-*a*" to --FIGS. 12-*a*-- |
| COLUMN 7, | LINES 43-44, | change "strip comprises" to --flexible strip 54 comprises-- |
| COLUMN 7, | LINE 57, | change "strap 51, (FIG. 5)," to --strap 51 (FIG. 5),-- |
| COLUMN 8, | LINE 30, | change "FIG. 9-*a*" to --FIGS. 9-*a*-- |

Signed and Sealed this
Twenty-third Day of August, 2016

Michelle K. Lee
*Director of the United States Patent and Trademark Office*